(12) United States Patent
Kaiser et al.

(10) Patent No.: US 7,776,077 B2
(45) Date of Patent: Aug. 17, 2010

(54) METHOD FOR SOFT TISSUE ATTACHMENT

(75) Inventors: Ryan A. Kaiser, Leesburg, IN (US);
Kevin T. Stone, Winona Lake, IN (US);
Stephen M. Howell, Elk Grove, CA (US)

(73) Assignee: Biomet Sports Medicince, LLC, Warsaw, IN (US)

( * ) Notice: Subject to any disclaimer, the term of this patent is extended or adjusted under 35 U.S.C. 154(b) by 39 days.

(21) Appl. No.: 12/047,048

(22) Filed: Mar. 12, 2008

(65) Prior Publication Data
US 2008/0161852 A1 Jul. 3, 2008

Related U.S. Application Data

(62) Division of application No. 10/864,905, filed on Jun. 9, 2004.

(51) Int. Cl.
*A61B 17/04* (2006.01)
(52) U.S. Cl. ..................................................... 606/300
(58) Field of Classification Search ................ 606/232, 606/233, 300, 321; 411/340–346
See application file for complete search history.

(56) References Cited

U.S. PATENT DOCUMENTS

| 65,499 | A | 6/1867 | Miller |
| 401,659 | A | 4/1889 | Remington |
| 838,203 | A | 12/1906 | Neil |
| 939,921 | A | 11/1909 | Moeller |
| 1,077,006 | A | 10/1913 | Smith |
| 1,340,470 | A | 5/1920 | Whitmore |
| 1,386,202 | A | 8/1921 | Peterson |
| 1,572,289 | A | 2/1926 | Hogan |
| 2,061,385 | A | 11/1936 | Nadler |
| 2,065,659 | A | 12/1936 | Cullen |
| 2,121,193 | A | 6/1938 | Hanicke |
| 2,242,003 | A | 5/1941 | Lorenzo |
| 2,267,925 | A | 12/1941 | Johnston |
| 2,329,398 | A | 9/1943 | Duffy |
| 2,562,419 | A | 7/1951 | Ferris |
| 2,600,395 | A | 6/1952 | Domoj et al. |
| 2,665,597 | A | 1/1954 | Hill |
| 2,698,986 | A | 1/1955 | Brown |

(Continued)

FOREIGN PATENT DOCUMENTS

DE 2529669 3/1976

(Continued)

OTHER PUBLICATIONS

"Ez Loc Femoral Fixation Device," copyright 2005 Arthrotek, Inc. (8 sheets).

(Continued)

*Primary Examiner*—Thomas C Barrett
*Assistant Examiner*—Nicholas Woodall
(74) *Attorney, Agent, or Firm*—Harness, Dickey

(57) ABSTRACT

An apparatus and method for fixing a selected graft relative to a selected anatomical portion. An anchor may be provided that may be interconnected with a selected graft portion that is operable to pass through a selected bore and then moved into an operable position to engage a selected portion of the bore to substantially eliminate the possibility of the graft moving in an unselected direction through the bore.

22 Claims, 5 Drawing Sheets

U.S. PATENT DOCUMENTS

| | | |
|---|---|---|
| 2,883,096 A | 4/1959 | Dawson |
| 3,003,155 A | 10/1961 | Mielzynski et al. |
| 3,093,220 A | 6/1963 | Modrey |
| 3,123,077 A | 3/1964 | Alcamo |
| 3,168,850 A | 2/1965 | Tennican |
| 3,399,432 A | 9/1968 | Merser |
| 3,435,475 A | 4/1969 | Bisk |
| 3,470,834 A | 10/1969 | Bone |
| 3,500,820 A | 3/1970 | Almen |
| 3,513,484 A | 5/1970 | Hausner |
| 3,527,223 A | 9/1970 | Shein |
| 3,541,591 A | 11/1970 | Hoegerman |
| 3,664,345 A | 5/1972 | Dabbs et al. |
| 3,665,560 A | 5/1972 | Bennett et al. |
| 3,683,422 A | 8/1972 | Stemmer et al. |
| 3,695,271 A | 10/1972 | Chodorow |
| 3,699,969 A | 10/1972 | Allen |
| 3,716,058 A | 2/1973 | Tanner, Jr. |
| 3,744,488 A | 7/1973 | Cox |
| 3,845,772 A | 11/1974 | Smith |
| 3,871,368 A | 3/1975 | Johnson et al. |
| 3,875,648 A | 4/1975 | Bone |
| 3,896,500 A | 7/1975 | Rambert et al. |
| 3,910,281 A | 10/1975 | Kletschka et al. |
| 3,931,667 A | 1/1976 | Merser et al. |
| 3,943,932 A | 3/1976 | Woo |
| 3,953,896 A | 5/1976 | Treace |
| 3,976,079 A | 8/1976 | Samuels et al. |
| 3,990,619 A | 11/1976 | Russell |
| 4,006,747 A | 2/1977 | Kronenthal et al. |
| 4,013,071 A | 3/1977 | Rosenberg |
| 4,085,466 A | 4/1978 | Goodfellow et al. |
| 4,149,277 A | 4/1979 | Bokros |
| 4,185,636 A | 1/1980 | Gabbay et al. |
| 4,210,148 A | 7/1980 | Stivala |
| 4,235,238 A | 11/1980 | Ogiu et al. |
| 4,243,037 A | 1/1981 | Smith |
| 4,273,117 A | 6/1981 | Neuhauser et al. |
| 4,275,717 A | 6/1981 | Bolesky |
| 4,287,807 A | 9/1981 | Pacharis et al. |
| 4,291,698 A | 9/1981 | Fuchs et al. |
| 4,301,551 A | 11/1981 | Dore et al. |
| 4,326,531 A | 4/1982 | Shimonaka et al. |
| 4,388,921 A | 6/1983 | Sutter et al. |
| 4,400,833 A | 8/1983 | Kurland |
| 4,409,974 A | 10/1983 | Freedland |
| 4,454,875 A | 6/1984 | Pratt et al. |
| 4,462,395 A | 7/1984 | Johnson |
| 4,463,753 A | 8/1984 | Gustilo |
| 4,473,102 A | 9/1984 | Ohman et al. |
| 4,493,323 A | 1/1985 | Albright et al. |
| 4,496,468 A | 1/1985 | House et al. |
| 4,532,926 A | 8/1985 | O'Holla |
| 4,537,185 A | 8/1985 | Stednitz |
| 4,573,844 A | 3/1986 | Smith |
| 4,576,608 A | 3/1986 | Homsy |
| 4,584,722 A | 4/1986 | Levy et al. |
| 4,590,928 A | 5/1986 | Hunt et al. |
| 4,602,635 A | 7/1986 | Mulhollan et al. |
| 4,605,414 A | 8/1986 | Czajka |
| 4,621,640 A | 11/1986 | Mulhollan et al. |
| 4,632,100 A | 12/1986 | Somers et al. |
| 4,649,952 A | 3/1987 | Jobe |
| 4,653,486 A | 3/1987 | Coker |
| 4,655,777 A | 4/1987 | Dunn et al. |
| 4,667,675 A | 5/1987 | Davis |
| 4,669,473 A | 6/1987 | Richards et al. |
| 4,688,561 A | 8/1987 | Reese |
| 4,690,169 A | 9/1987 | Jobe |
| 4,708,132 A | 11/1987 | Silvestrini |
| 4,719,671 A | 1/1988 | Ito et al. |
| 4,728,332 A | 3/1988 | Albrektsson et al. |
| 4,738,255 A | 4/1988 | Goble et al. |
| 4,741,330 A | 5/1988 | Hayhurst |
| 4,744,353 A | 5/1988 | McFarland |
| 4,744,793 A | 5/1988 | Parr et al. |
| 4,750,492 A | 6/1988 | Jacobs |
| 4,772,286 A | 9/1988 | Goble et al. |
| 4,773,910 A | 9/1988 | Chen et al. |
| 4,775,380 A | 10/1988 | Seedhom et al. |
| 4,776,328 A | 10/1988 | Frey et al. |
| 4,823,794 A | 4/1989 | Pierce |
| 4,828,562 A | 5/1989 | Kenna |
| 4,851,005 A | 7/1989 | Hunt et al. |
| 4,863,383 A | 9/1989 | Grafelmann et al. |
| 4,870,957 A | 10/1989 | Goble et al. |
| 4,893,619 A | 1/1990 | Dale et al. |
| 4,895,148 A | 1/1990 | Bays et al. |
| 4,896,668 A | 1/1990 | Popoff et al. |
| 4,898,156 A | 2/1990 | Gatturna et al. |
| 4,927,421 A | 5/1990 | Goble et al. |
| 4,946,468 A | 8/1990 | Li |
| 4,950,270 A | 8/1990 | Bowman et al. |
| 4,961,741 A | 10/1990 | Hayhurst |
| 4,968,315 A | 11/1990 | Gatturna |
| 4,979,956 A | 12/1990 | Silvestrini |
| 4,988,351 A | 1/1991 | Paulos et al. |
| 4,997,433 A | 3/1991 | Goble et al. |
| 5,002,550 A | 3/1991 | Li |
| 5,037,422 A | 8/1991 | Hayhurst et al. |
| 5,046,513 A | 9/1991 | Gatturna et al. |
| 5,062,344 A | 11/1991 | Gerker |
| 5,062,843 A | 11/1991 | Mahony, III |
| 5,078,731 A | 1/1992 | Hayhurst |
| 5,078,843 A | 1/1992 | Pratt |
| 5,084,050 A | 1/1992 | Draenert et al. |
| 5,092,866 A | 3/1992 | Breard et al. |
| 5,098,433 A * | 3/1992 | Freedland .................... 606/63 |
| 5,100,415 A | 3/1992 | Hayhurst |
| 5,100,417 A | 3/1992 | Cerier et al. |
| 5,116,337 A | 5/1992 | Johnson |
| 5,116,373 A | 5/1992 | Jakob et al. |
| 5,116,375 A | 5/1992 | Hofmann |
| 5,127,785 A | 7/1992 | Faucher et al. |
| 5,129,902 A | 7/1992 | Goble et al. |
| 5,129,906 A | 7/1992 | Ross et al. |
| 5,139,520 A | 8/1992 | Rosenberg |
| 5,147,362 A | 9/1992 | Goble |
| 5,152,790 A | 10/1992 | Rosenberg et al. |
| 5,156,616 A | 10/1992 | Meadows et al. |
| D331,626 S | 12/1992 | Hayhurst et al. |
| 5,176,682 A | 1/1993 | Chow |
| 5,197,987 A | 3/1993 | Koch et al. |
| 5,203,787 A | 4/1993 | Noblitt et al. |
| 5,207,679 A | 5/1993 | Li |
| 5,209,753 A | 5/1993 | Biedermann et al. |
| 5,211,647 A | 5/1993 | Schmieding |
| 5,224,946 A | 7/1993 | Hayhurst et al. |
| 5,234,435 A | 8/1993 | Seagrave, Jr. |
| 5,235,461 A | 8/1993 | Kirsch et al. |
| 5,236,445 A | 8/1993 | Hayhurst et al. |
| 5,236,461 A | 8/1993 | Forte |
| 5,246,441 A | 9/1993 | Ross et al. |
| 5,258,016 A | 11/1993 | DiPoto et al. |
| 5,258,040 A | 11/1993 | Bruchman et al. |
| 5,268,001 A | 12/1993 | Nicholson et al. |
| 5,269,783 A | 12/1993 | Sander |
| 5,269,809 A | 12/1993 | Hayhurst et al. |
| 5,281,422 A | 1/1994 | Badylak et al. |
| 5,282,809 A | 2/1994 | Kammerer et al. |
| 5,282,832 A | 2/1994 | Toso et al. |
| 5,285,040 A | 2/1994 | Brandberg et al. |
| 5,290,217 A | 3/1994 | Campos |
| 5,306,301 A | 4/1994 | Graf et al. |

| | | | | | | |
|---|---|---|---|---|---|---|
| 5,320,115 | A | 6/1994 | Kenna | 5,769,894 | A | 6/1998 | Ferragamo |
| 5,320,626 | A | 6/1994 | Schmieding | 5,782,864 | A | 7/1998 | Lizardi |
| 5,324,308 | A | 6/1994 | Pierce | 5,782,866 | A | 7/1998 | Wenstrom, Jr. |
| 5,336,240 | A | 8/1994 | Metzler et al. | 5,785,714 | A | 7/1998 | Morgan et al. |
| 5,356,413 | A | 10/1994 | Martins et al. | 5,810,848 | A | 9/1998 | Hayhurst |
| 5,362,294 | A | 11/1994 | Seitzinger | 5,814,070 | A | 9/1998 | Borzone et al. |
| 5,370,661 | A | 12/1994 | Branch | 5,824,011 | A | 10/1998 | Stone et al. |
| 5,370,662 | A | 12/1994 | Stone et al. | 5,868,789 | A | 2/1999 | Huebner |
| 5,372,146 | A | 12/1994 | Branch | 5,885,294 | A | 3/1999 | Pedlick et al. |
| 5,372,604 | A | 12/1994 | Trott | 5,899,938 | A | 5/1999 | Sklar et al. |
| 5,372,821 | A | 12/1994 | Badylak et al. | 5,911,721 | A | 6/1999 | Nicholson et al. |
| 5,379,492 | A | 1/1995 | Glesser | 5,918,604 | A | 7/1999 | Whelan |
| 5,383,878 | A | 1/1995 | Roger et al. | 5,931,838 | A | 8/1999 | Vito |
| 5,391,171 | A | 2/1995 | Schmieding | 5,931,869 | A | 8/1999 | Boucher et al. |
| 5,393,302 | A | 2/1995 | Clark et al. | 5,951,559 | A | 9/1999 | Burkhart |
| RE34,871 | E | 3/1995 | McGuire et al. | 5,957,953 | A | 9/1999 | DiPoto et al. |
| 5,417,691 | A | 5/1995 | Hayhurst | 5,964,764 | A | 10/1999 | West, Jr. et al. |
| 5,417,712 | A | 5/1995 | Whittaker et al. | 5,964,783 | A | 10/1999 | Grafton et al. |
| 5,423,823 | A | 6/1995 | Schmieding | 5,980,558 | A | 11/1999 | Wiley |
| 5,423,860 | A | 6/1995 | Lizardi et al. | 5,980,559 | A | 11/1999 | Bonutti |
| 5,425,733 | A | 6/1995 | Schmieding | 6,010,525 | A | 1/2000 | Bonutti et al. |
| 5,443,468 | A | 8/1995 | Johnson | 6,027,523 | A | 2/2000 | Schmieding |
| 5,443,482 | A | 8/1995 | Stone et al. | 6,045,573 | A | 4/2000 | Wenstrom, Jr. et al. |
| 5,445,833 | A | 8/1995 | Badylak et al. | 6,056,752 | A | 5/2000 | Roger et al. |
| 5,451,203 | A | 9/1995 | Lamb | 6,062,344 | A | 5/2000 | Okabe et al. |
| 5,454,811 | A | 10/1995 | Huebner | 6,086,591 | A | 7/2000 | Bojarski |
| 5,456,685 | A | 10/1995 | Huebner | 6,086,592 | A | 7/2000 | Rosenberg et al. |
| 5,458,601 | A | 10/1995 | Young, Jr. et al. | 6,086,608 | A | 7/2000 | Ek et al. |
| 5,458,604 | A | 10/1995 | Schmieding | 6,099,530 | A | 8/2000 | Simonian et al. |
| 5,464,427 | A | 11/1995 | Curtis et al. | 6,099,568 | A | 8/2000 | Simonian et al. |
| 5,464,440 | A | 11/1995 | Johansson et al. | 6,132,433 | A | 10/2000 | Whelan |
| 5,470,334 | A | 11/1995 | Ross et al. | 6,132,437 | A | 10/2000 | Omurtag et al. |
| 5,472,452 | A | 12/1995 | Trott | 6,139,565 | A | 10/2000 | Stone et al. |
| 5,474,572 | A | 12/1995 | Hayhurst | 6,146,408 | A | 11/2000 | Bartlett |
| 5,480,403 | A | 1/1996 | Lee et al. | 6,152,928 | A | 11/2000 | Wenstrom, Jr. |
| 5,486,197 | A | 1/1996 | Le et al. | 6,156,039 | A | 12/2000 | Thal |
| 5,500,000 | A | 3/1996 | Feagin et al. | 6,159,234 | A | 12/2000 | Bonutti et al. |
| 5,520,691 | A | 5/1996 | Branch | 6,165,203 | A | 12/2000 | Krebs |
| 5,522,817 | A | 6/1996 | Sander et al. | 6,168,598 | B1 | 1/2001 | Martello |
| 5,522,844 | A | 6/1996 | Johnson | 6,168,628 | B1 | 1/2001 | Huebner |
| 5,522,845 | A | 6/1996 | Wenstrom, Jr. | 6,187,025 | B1 | 2/2001 | Machek |
| 5,524,946 | A | 6/1996 | Thompson | 6,193,754 | B1 | 2/2001 | Seedhom et al. |
| 5,527,342 | A | 6/1996 | Pietrzak et al. | 6,200,329 | B1 | 3/2001 | Fung et al. |
| 5,540,718 | A | 7/1996 | Bartlett | 6,203,572 | B1 | 3/2001 | Johnson et al. |
| 5,549,613 | A | 8/1996 | Goble et al. | 6,221,107 | B1 | 4/2001 | Steiner et al. |
| 5,573,548 | A | 11/1996 | Nazre et al. | 6,231,592 | B1 | 5/2001 | Bonutti et al. |
| 5,584,695 | A | 12/1996 | Lal Sachdeva et al. | 6,235,057 | B1 | 5/2001 | Roger et al. |
| 5,584,835 | A | 12/1996 | Greenfield | 6,241,747 | B1 | 6/2001 | Ruff |
| 5,593,425 | A | 1/1997 | Bonutti et al. | 6,267,766 | B1 | 7/2001 | Burkhart |
| 5,601,557 | A | 2/1997 | Hayhurst | 6,283,996 | B1 | 9/2001 | Chervitz et al. |
| 5,603,716 | A | 2/1997 | Morgan et al. | 6,296,659 | B1 | 10/2001 | Foerster |
| 5,628,756 | A | 5/1997 | Barker, Jr. et al. | 6,319,271 | B1 | 11/2001 | Schwartz et al. |
| 5,628,766 | A | 5/1997 | Johnson | 6,371,124 | B1 | 4/2002 | Whelan |
| 5,630,824 | A | 5/1997 | Hart | 6,387,129 | B2 | 5/2002 | Rieser et al. |
| 5,632,748 | A | 5/1997 | Beck, Jr. et al. | 6,436,124 | B1 | 8/2002 | Anderson et al. |
| 5,643,266 | A | 7/1997 | Li | 6,440,134 | B1 | 8/2002 | Zaccherotti et al. |
| 5,643,320 | A | 7/1997 | Lower et al. | 6,451,030 | B2 | 9/2002 | Li et al. |
| 5,643,321 | A | 7/1997 | McDevitt | 6,482,210 | B1 | 11/2002 | Skiba et al. |
| 5,645,568 | A | 7/1997 | Chervitz et al. | 6,508,830 | B2 | 1/2003 | Steiner |
| 5,645,588 | A | 7/1997 | Graf et al. | 6,511,499 | B2 | 1/2003 | Schmieding et al. |
| 5,647,874 | A | 7/1997 | Hayhurst | 6,517,578 | B2 | 2/2003 | Hein et al. |
| 5,649,963 | A | 7/1997 | McDevitt | 6,527,795 | B1 | 3/2003 | Lizardi |
| 5,662,658 | A | 9/1997 | Wenstrom, Jr. | 6,533,802 | B2 | 3/2003 | Bojarski et al. |
| 5,671,695 | A | 9/1997 | Schroeder | 6,537,319 | B2 | 3/2003 | Whelan |
| 5,674,224 | A | 10/1997 | Howell et al. | 6,540,750 | B2 | 4/2003 | Burkhart |
| 5,681,352 | A | 10/1997 | Clancy, III et al. | 6,544,281 | B2 | 4/2003 | ElAttrache et al. |
| 5,690,676 | A | 11/1997 | DiPoto et al. | 6,551,343 | B1 | 4/2003 | Tormala et al. |
| 5,699,657 | A | 12/1997 | Paulson | 6,553,802 | B1 | 4/2003 | Jacob et al. |
| 5,713,005 | A | 1/1998 | Proebsting | 6,554,862 | B2 | 4/2003 | Hays et al. |
| 5,713,905 | A | 2/1998 | Goble et al. | 6,579,295 | B1 | 6/2003 | Supinski |
| 5,733,307 | A | 3/1998 | Dinsdale | 6,585,730 | B1 | 7/2003 | Foerster |
| 5,766,221 | A * | 6/1998 | Benderev et al. ............ 606/232 | 6,589,245 | B1 | 7/2003 | Weiler et al. |
| 5,766,250 | A | 6/1998 | Chervitz et al. | 6,599,289 | B1 | 7/2003 | Bojarski et al. |

| | | |
|---|---|---|
| 6,616,694 B1 | 9/2003 | Hart |
| 6,620,329 B2 | 9/2003 | Rosen et al. |
| 6,623,524 B2 | 9/2003 | Schmieding |
| 6,626,910 B1 | 9/2003 | Hugues et al. |
| 6,626,919 B1 | 9/2003 | Swanstrom |
| 6,641,596 B1 | 11/2003 | Lizardi |
| 6,641,597 B2 | 11/2003 | Burkhart et al. |
| 6,645,227 B2 | 11/2003 | Fallin et al. |
| 6,652,563 B2 | 11/2003 | Dreyfuss |
| 6,656,182 B1 | 12/2003 | Hayhurst |
| 6,682,549 B2 | 1/2004 | Bartlett |
| 6,685,728 B2 | 2/2004 | Sinnott et al. |
| 6,689,154 B2 | 2/2004 | Bartlett |
| 6,692,499 B2 | 2/2004 | Tormala et al. |
| 6,712,849 B2 | 3/2004 | Re et al. |
| 6,730,092 B2 | 5/2004 | Songer |
| 6,773,450 B2 | 8/2004 | Leung et al. |
| 6,780,190 B2 | 8/2004 | Maroney |
| 6,802,862 B1 | 10/2004 | Roger et al. |
| 6,833,005 B1 | 12/2004 | Mantas et al. |
| 6,840,953 B2 | 1/2005 | Martinek |
| 6,863,671 B1 | 3/2005 | Strobel et al. |
| 6,887,259 B2 | 5/2005 | Lizardi |
| 6,902,573 B2 | 6/2005 | Strobel et al. |
| 6,916,321 B2 | 7/2005 | TenHuisen et al. |
| 6,923,823 B1 | 8/2005 | Bartlett et al. |
| 6,923,824 B2 | 8/2005 | Morgan et al. |
| 6,972,027 B2 | 12/2005 | Fallin et al. |
| 6,986,781 B2 | 1/2006 | Smith |
| 7,097,654 B1 | 8/2006 | Freedland |
| 2001/0014825 A1 | 8/2001 | Burke et al. |
| 2001/0037131 A1 | 11/2001 | Schmieding et al. |
| 2001/0037153 A1 | 11/2001 | Rockwood et al. |
| 2001/0041937 A1 | 11/2001 | Rieser et al. |
| 2001/0041938 A1 | 11/2001 | Hein |
| 2001/0044639 A1 | 11/2001 | Levinson |
| 2001/0047206 A1 | 11/2001 | Sklar et al. |
| 2001/0053934 A1 | 12/2001 | Schmieding |
| 2002/0001964 A1 | 1/2002 | Choi |
| 2002/0004669 A1 | 1/2002 | Bartlett |
| 2002/0007182 A1 | 1/2002 | Kim |
| 2002/0010513 A1 | 1/2002 | Schmieding |
| 2002/0013608 A1 | 1/2002 | ElAttrache et al. |
| 2002/0099411 A1 | 7/2002 | Bartlett |
| 2002/0111653 A1 | 8/2002 | Foerster |
| 2002/0120292 A1 | 8/2002 | Morgan |
| 2002/0128684 A1 | 9/2002 | Foerster |
| 2002/0147463 A1 | 10/2002 | Martinek |
| 2002/0161401 A1 | 10/2002 | Steiner |
| 2002/0161439 A1 | 10/2002 | Strobel et al. |
| 2002/0173788 A1 | 11/2002 | Bojarski et al. |
| 2002/0188298 A1 | 12/2002 | Chan |
| 2003/0023268 A1 | 1/2003 | Lizardi |
| 2003/0088272 A1 | 5/2003 | Smith |
| 2003/0120309 A1 | 6/2003 | Colleran et al. |
| 2003/0130694 A1 | 7/2003 | Bojarski et al. |
| 2003/0135239 A1 | 7/2003 | Gabriel et al. |
| 2003/0135963 A1 | 7/2003 | Holbrook et al. |
| 2003/0167072 A1 | 9/2003 | Oberlander |
| 2003/0167090 A1 | 9/2003 | Chervitz et al. |
| 2003/0176865 A1 | 9/2003 | Supinski |
| 2003/0176919 A1 | 9/2003 | Schmieding |
| 2004/0015171 A1 | 1/2004 | Bojarski et al. |
| 2004/0092936 A1* | 5/2004 | Miller et al. .................. 606/72 |
| 2004/0098051 A1 | 5/2004 | Fallin et al. |
| 2004/0138706 A1 | 7/2004 | Abrams et al. |
| 2004/0147929 A1 | 7/2004 | Biedermann et al. |
| 2004/0153153 A1 | 8/2004 | Elson et al. |
| 2004/0162579 A1 | 8/2004 | Foerster |
| 2004/0243178 A1 | 12/2004 | Haut et al. |
| 2005/0038426 A1 | 2/2005 | Chan |
| 2005/0096696 A1 | 5/2005 | Forsberg |
| 2005/0096697 A1 | 5/2005 | Forsberg et al. |
| 2005/0107828 A1 | 5/2005 | Reese |
| 2005/0119531 A1 | 6/2005 | Sharratt |
| 2005/0222618 A1 | 10/2005 | Dreyfuss et al. |
| 2005/0222619 A1 | 10/2005 | Dreyfuss et al. |
| 2005/0267479 A1 | 12/2005 | Morgan et al. |
| 2005/0277961 A1 | 12/2005 | Stone et al. |
| 2005/0283156 A1 | 12/2005 | Schmieding et al. |
| 2005/0283158 A1 | 12/2005 | West |
| 2006/0079904 A1 | 4/2006 | Thal |
| 2007/0016305 A1 | 1/2007 | Chudik |
| 2007/0049944 A1 | 3/2007 | Stone et al. |
| 2007/0225719 A1 | 9/2007 | Stone et al. |

FOREIGN PATENT DOCUMENTS

| | | |
|---|---|---|
| DE | 2747312 | 4/1979 |
| DE | 2818254 | 10/1979 |
| DE | 4127550 | 2/1993 |
| EP | 0129442 | 12/1984 |
| EP | 0172130 | 2/1986 |
| EP | 0241240 | 10/1987 |
| EP | 0241792 | 10/1987 |
| EP | 0260970 | 3/1988 |
| EP | 0270704 | 6/1988 |
| EP | 0282789 | 9/1988 |
| EP | 0317406 | 5/1989 |
| EP | 0340159 | 11/1989 |
| EP | 0346183 | 12/1989 |
| EP | 0349173 | 1/1990 |
| EP | 0374088 | 6/1990 |
| EP | 0409364 | 1/1991 |
| EP | 0415915 | 3/1991 |
| EP | 0451932 | 10/1991 |
| EP | 0464480 | 1/1992 |
| EP | 0497079 | 8/1992 |
| EP | 0502509 | 9/1992 |
| EP | 520177 | 12/1992 |
| EP | 0520177 | 12/1992 |
| EP | 0546726 | 6/1993 |
| EP | 0574707 | 12/1993 |
| EP | 0582514 | 2/1994 |
| EP | 0591991 | 4/1994 |
| EP | 0627203 | 12/1994 |
| FR | 2622790 | 5/1989 |
| FR | 2655840 | 6/1991 |
| FR | 2682867 | 4/1993 |
| FR | 2687911 | 9/1993 |
| FR | 2688689 | 9/1993 |
| FR | 2704140 | 10/1994 |
| GB | 1413477 | 11/1975 |
| GB | 1485681 | 9/1977 |
| GB | 2118474 | 11/1983 |
| GB | 2227175 | 7/1990 |
| GB | 2253147 | 9/1992 |
| JP | 5300917 | 11/1993 |
| WO | WO-8603666 | 7/1986 |
| WO | WO-8901767 | 3/1989 |
| WO | WO-8909030 | 10/1989 |
| WO | WO-8910096 | 11/1989 |
| WO | WO-9008510 | 8/1990 |
| WO | WO-9203980 | 3/1992 |
| WO | WO-9314705 | 8/1993 |
| WO | WO-9529637 | 11/1995 |
| WO | WO-9532670 | 12/1995 |
| WO | WO-9629029 | 9/1996 |
| WO | WO-9812991 | 4/1998 |
| WO | WO-9812992 | 4/1998 |

OTHER PUBLICATIONS

"SE Graft Tensioning System Surgical Technique," Linvatec Corporation copyright 2003, 2004.

"Technique for ACL Reconstruction with Acufex Director Drill Guide and Endobutton CL," by Thomas D. Roseberg, copyright 1999 Smith & Nephew.

Bio-Intrafix (TCP/PLA & Intrafix, Tibial Soft Tissue Fasteners, by DePuy Mitek, 6 sheets, (date unknown).

* cited by examiner

METHOD FOR SOFT TISSUE ATTACHMENT

CROSS-REFERENCE TO RELATED APPLICATIONS

This application is a divisional of U.S. patent application Ser. No. 10/864,905 filed on Jun. 9, 2004. The disclosure of the above application is incorporated herein by reference.

FIELD

The present application relates generally to orthopedic procedures; and relates particularly to orthopedic procedures for interconnecting soft tissue to a bony portion of an anatomy.

BACKGROUND

In an anatomy, for example a human anatomy, various soft tissue portions are interconnected with various bony portions. For example, a tendon may interconnect a selected muscle group with a selected portion of the anatomy. Similarly, a ligament may interconnect two bony portions. For example, the anterior cruciate ligament interconnects a portion of the tibia with a portion of the femur. Although the natural and healthy anatomy generally is able to support the various portions of the anatomy with the natural ligaments and tendons, and other selected soft tissues, injury, age, or other circumstances may cause the weakening or breaking of various soft tissue portions.

For example, a strain, other injury, or disease may weaken various soft tissue portions, such as the anterior cruciate ligament (ACL). The breaking or weakening of the tissue may require the tissue to be reconnected or replaced with various autographs or xenographs that may be made of natural or synthetic materials. These various materials are generally interconnected with selected portions of the anatomy using screws or other similar friction or obstruction holding devices.

Though various procedures and instruments may allow for interconnection of soft tissue with selected bony portions, it may be desirable to perform a procedure substantially percutaneously or through a small incision or in less time. Generally, the screws or the obstruction devices must be driven into the selected bony portion to hold the selected soft tissue in the appropriate location. The procedure must be planned and executed in a particular manner to insure that appropriate fixation of the soft tissue to the selected bony portion. Therefore, it may be desirable to provide an instrument and method that allows for a substantially quick implantation or connection of a selected soft tissue graft or soft tissue portion to a selected bony portion.

SUMMARY

A device for connecting or holding a soft tissue graft relative to a selected anatomical portion such as a bone portion. An anchor may be provided that is operably interconnected with a selected portion of the graft and the anchor may anchor the connection portion to the selected bony portion. For example, the anchor portion may be passed through a bore and manipulated to hold the soft tissue graft relative to the bore by providing an interference fit with a portion of the bone next to or relative to the bore. The anchor may be formed as substantially a single piece or may be an assembly of a plurality of pieces, such that the anchor may pass through the bore and may be manipulated to interfere with passing in an opposite direction through the bore again.

According to various embodiments a soft tissue anchor assembly includes a body extending along a first axis including a first end and a second end. A lever arm is rotatably interconnected with the body inbound from the first end of the body, movable between an activated and a non-activated position. An interconnection region is spaced a distance from the first end towards the second end of the body. The lever arm rotates relative to the body at an end of the lever arm.

According to various embodiments a soft tissue connection assembly that is operable to hold a soft tissue graft near a select portion of an anatomy comprises an anchor member to selectively engage the selected portion of the anatomy. The anchor member includes a lever arm and an engaging portion extending from the lever arm. The soft tissue interconnects with the engaging portion to be substantially held in a selected position relative to the selected portion of the anatomy with the spacer member.

According to various embodiments a method of fixing a graft in a selected region of an anatomy with an anchor member includes forming a bore in the selected region of the anatomy thereby defining an interior surface within the bore and an exterior surface outside of the bore. The graft may be associated with the anchor member and passed through the anchor member through a selected portion of the bore to a first position in a first orientation. The anchor member may be moved to a second position thereby selectively engaging the exterior surface.

Further areas of applicability will become apparent from the detailed description provided hereinafter. It should be understood that the detailed description and various examples, while indicating the various embodiments, are intended for purposes of illustration only and are not intended to limit the scope.

BRIEF DESCRIPTION OF THE DRAWINGS

The present description and appended claims will become more fully understood from the detailed description and the accompanying drawings, wherein:

DETAILED DESCRIPTION OF VARIOUS EMBODIMENTS

Figure 1:
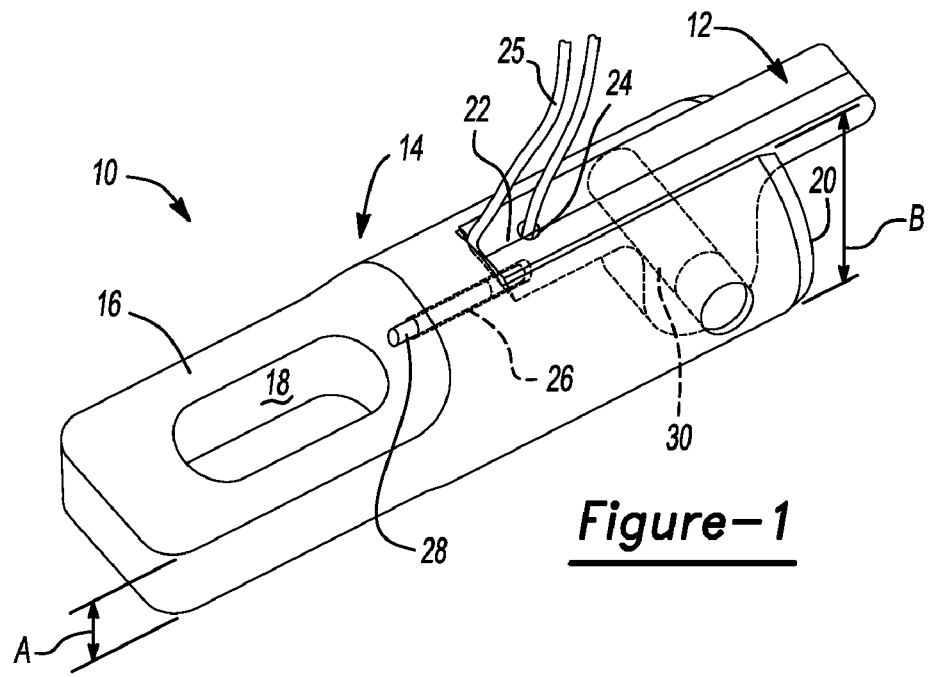
FIG. 1 is a top perspective view of an anchor according to various embodiments in an unactivated position.

The following description of various embodiments is merely exemplary in nature and is in no way intended to limit the invention, its application, or uses. Although the following description may relate to providing a soft tissue attachment relative to a femur, such as for an anterior cruciate ligament (ACL) fixation, the various apparati and methods may be used for a plurality of procedures. For example, the various instruments may be used to affix or hold a hamstring, Achilles tendon allograft, other soft tissue, or any other appropriate portion. In addition, although various embodiments may be illustrated to be interconnected with a selected graft using a flexible strand, such as a suture, it will be understood that a graft may be affixed directly to an implant member. Also, the anchor, according to various embodiments, may be used to anchor any appropriate portion, such as a soft tissue, suture, various implements, or any appropriate portion. Therefore, it will be understood that the following description is merely exemplary of various embodiments and is not intended to be limiting.

An anchor may be formed as a plurality or assembly of portions that may be operably interconnected and manipulated to perform a selected task, such as providing an anchor for a selected portion. For example, with reference to FIG. 1, an anchor 10 may be used to anchor a selected portion, such as a soft tissue, other tissue, implant, flexible strand, or other appropriate portion to a portion of an anatomy. The anchor 10 generally includes a lever arm or manipulable portion or region 12 that is interconnected with a main body or soft tissue engaging portion 14.

Extending from a first end of the body 14 is a soft tissue or engaging portion 16. The soft tissue engaging portion 16 may define a bore 18 through which a soft tissue portion may be passed or affixed. This may allow for a selected portion of the anatomy, such as soft tissue, to be connected directly to the anchor 10.

The body 14 is generally formed as a substantially single piece that may be forged or milled from a single piece of material. The body 14 may be formed of any appropriate material such as metal formed of a single element or of an alloy, ceramics, polymers, any other appropriate material, or combinations thereof. Generally the body 14 is substantially rigid such that an anatomical or other force applied to the body 14 will not substantially deform the body 14. Nevertheless the body 14 may include a selected amount of deformability depending upon the specific application.

As discussed herein, the body 14 may include various cutouts and apertures to allow for interconnection, according to various embodiments, of portions with the anchor 10 and an anatomical portion. Therefore, the anchor 10 may be positioned relative to a selected portion of the anatomy without allowing for movement of the anchor 10 relative to the selected portion of the anatomy. It will be understood that the anchor 10 may be formed according to various embodiments, but may be formed of the substantially similar materials to provide substantially similar results.

Extending from a second end 20 of the body 14, or provided at the second end 20, is the lever portion 12. The lever portion 12 generally includes an actuation end 22 that includes a bore 24. Interconnected with the bore 24 may be an actuating member, such as a suture strand 25. Although, again it will be understood that any other appropriate mechanism or portion may be provided rather than the strand 25. As described herein, the strand 25 or the other appropriate portion may be provided to allow for insertion of the anchor 10 into a selected portion of the anatomy and for manipulating the actuation end 22. It will also be understood that the actuation end 22 may be formed in any appropriate matter and need not be substantially planar.

Also formed in the body 14 is a pin bore or region 26. Disposed in the pin bore 26 may be a pin 28. The pin 28 may selectively interconnect the body 14 and the lever arm 12, such that the lever arm 12 may be held substantially immobile relative to the body 14. The pin 28 may be interconnected to a selected portion, such as a release suture portion as described herein, or any other appropriate mechanism that may disengage the pin 28 from the lever arm 12.

Once the pin 28 is disengaged from the lever arm 12, as described further herein, the strand 25 may be used to actuate the lever arm 12 around an axis or fulcrum including a fulcrum or axle pin 30. The fulcrum pin 30 may interconnect the lever arm 12 with the body 14 for a selected purpose. The fulcrum pin 30 may generally be positioned on a fulcrum such that the lever 12 rotates relative to the fulcrum and is held relative to the body 14 with the fulcrum pin 30. Nevertheless, it will be understood that the lever arm 12 may be operable to move in any appropriate manner relative to the body 14. For example, the lever arm 12 may be provided to substantially slide, snap, swing, or move in any other appropriate manner from an unactivated position to an activated position. Therefore, it will be understood, according to various embodiments that the lever arm 12 may move in any appropriate manner from an unactivated position to an activated position. It will be understood that the lever arm may be positioned in the unactivated position to move the anchor 10 relative to a selected portion of the anatomy, or an anchoring position, and the lever arm 12 may then be moved to a second or activated position to substantially hold the anchor 10 in a selected position. It will be understood that the lever arm, according to various embodiments, may move relative to the body 14 and is not required to rotate.

When in the unactivated position, the actuation portion 22 of the lever arm 12 may be received within a recess or depression 31. Depression 31 may receive the lever arm 12 such that an external circumference or surface of the body 14 is substantially uninterrupted by the lever arm 12. The lever arm 12, or a portion thereof, may include a size or radius to allow it to be retained within the depression 31 without protruding past an exterior of the body 14. For example, the lever arm 12 may include an external radius substantially similar to that of the body 14 such that the depression 31 allows the lever arm 12 to substantially match the radius of the body 14. This may allow the anchor 10 to pass through a selected portion of the anatomy, such as a bore formed in the anatomy without being interrupted during its passage by the lever arm 12. As discussed herein, the body 14 may include a circumference that is substantially equivalent to a bore through which the anchor 10 may be passed.

As further described herein, the soft tissue engaging end 16, in which the bore 18 is formed, may include a dimension A that is less than a dimension B of the second end 20. As discussed further herein, the dimension A may allow for a substantially unobstructed passage of the anchor 10 through a bore formed in the anatomy for passing the anchor 10 through. This may be helpful in allowing the passage of the anchor 10 through the bore without binding or engaging the bore with the soft tissue; therefore, the dimension A may form a depression on both sides of the soft tissue engaging end 16 such that the dimension of the soft tissue in combination with the dimension A is less than or equivalent to the dimension B of the anchor. As discussed herein, the dimension B may include a diameter of the anchor body 14 that may be substantially equivalent to a diameter of the bore through which the anchor 10 may be passed.

Figure 2:
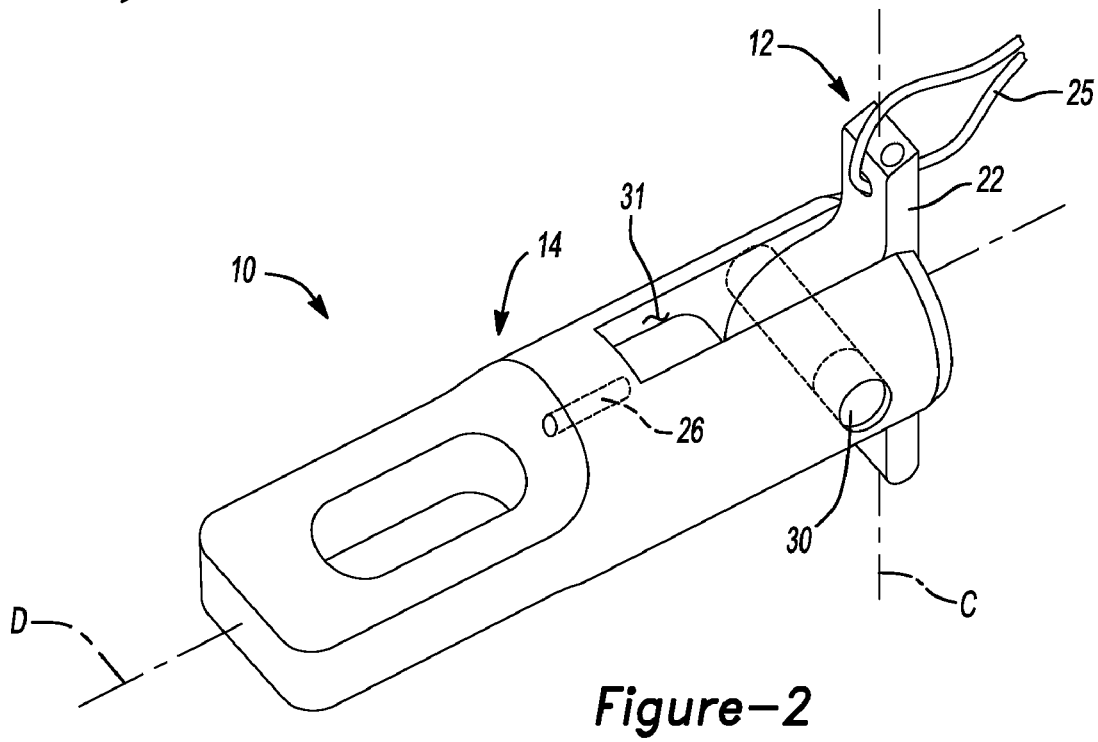
FIG. 2 is a top perspective view of an anchor of FIG. 1 in an activated position.

With reference to FIG. 2, the anchor 10 is shown in an activated position. In the activated position, the lever arm 12 defining an axis C may be substantially perpendicular to an axis D of the body 14. Therefore, the anchor 10 may be passed through a selected portion of the anatomy and activated with the strand 25. This moves or rotates the lever arm 12 relative to the body 14 to activate the lever arm 12, thereby allowing it to be provided generally perpendicular to axis D of the body 14. In the activated position, the length from a first end to a second end of the lever arm 12 may be greater than a length or diameter B of the body 14. As described herein, this may allow the anchor 10 to be passed through a portion smaller than the length of the lever arm 12 while the lever arm 12 may then be activated to hold the anchor 10 in a selected position.

Figure 3:
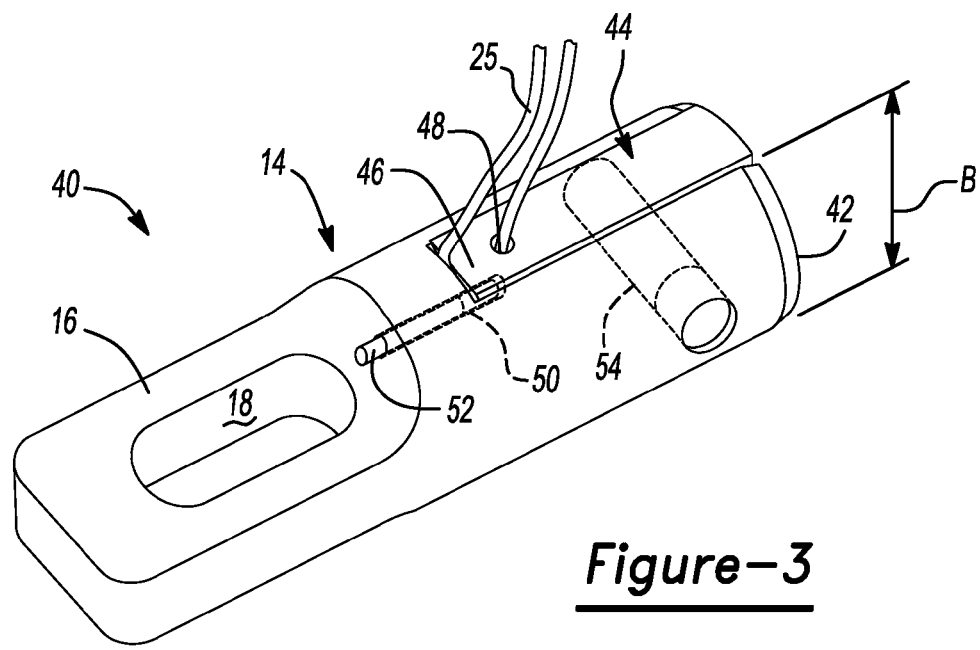
FIG. 3 is an anchor according to various embodiments in an unactivated position.

With reference to FIG. 3, an anchor 40 may be provided that includes portions similar to the anchor 10, illustrated in FIGS. 1 and 2, wherein like reference numerals are used to reference like portions. Although the anchor 40 may include similar portions, according to the various embodiments, to the various portions of the anchor 10, it will be understood that the anchor 40 need not be substantially similar to the anchor 10. Rather, the anchor 40, according to various embodiments, may include a body portion 14 that defines a soft tissue engaging or holding portion 16 that may define an engagement bore 18. The bore 18 may be provided to engage a selected soft tissue portion or other portion of the anatomy.

A second end 42 of the body 14 may be operably interconnected to a lever arm 44. The lever arm 44 may include an actuation portion 46 that defines a bore 48. As described above, a strand 25 may be provided to engage the bore 48 to assist in positioning the anchor 40 and in manipulating the lever arm 44. Also, a pin bore 50 may be provided through the body in which a pin 52 may be provided that may operably interconnect the body 14 and the lever arm 44. As discussed above, the pin 52 may be disengaged and this may allow the lever arm 44 to be moved to an operable position, for selected purposed.

The lever arm 44 may be generally rotatable about a pin 54, as described herein, generally a distance inbound form an end of the anchor 40. Nevertheless, the lever arm 44 generally does not extend beyond a length of the body 14 of the anchor 40. With continued reference to FIG. 3 and additional reference to FIG. 4, the anchor 40 may also include a recess 53 to receive the actuation region 46 of the lever arm 44. As discussed above, the depression 53 may allow for the anchor 40 to include a dimension B substantially equivalent along its entire length. This may be achieved by size, shape, etc. of the lever arm 44 and the depression 51. Therefore, as discussed above and further detailed herein, the anchor 40 may be passed through a selected portion of the anatomy and allow for substantially ease of passing due to the depression 53 allowing the actuation portion 46 of the lever arm 44 to be received therein. Therefore, in the unactivation position, the lever arm 44 may not disrupt the movement of the anchor 40 through a selected portion of the anatomy as described further herein. Moreover, it will be understood that the soft tissue engaging portion 16 may also include a depression such that the soft tissue portion that passes through the bore 18 will also not bind or disrupt passing of the anchor 40 through a selected portion of the anatomy.

Figure 4:
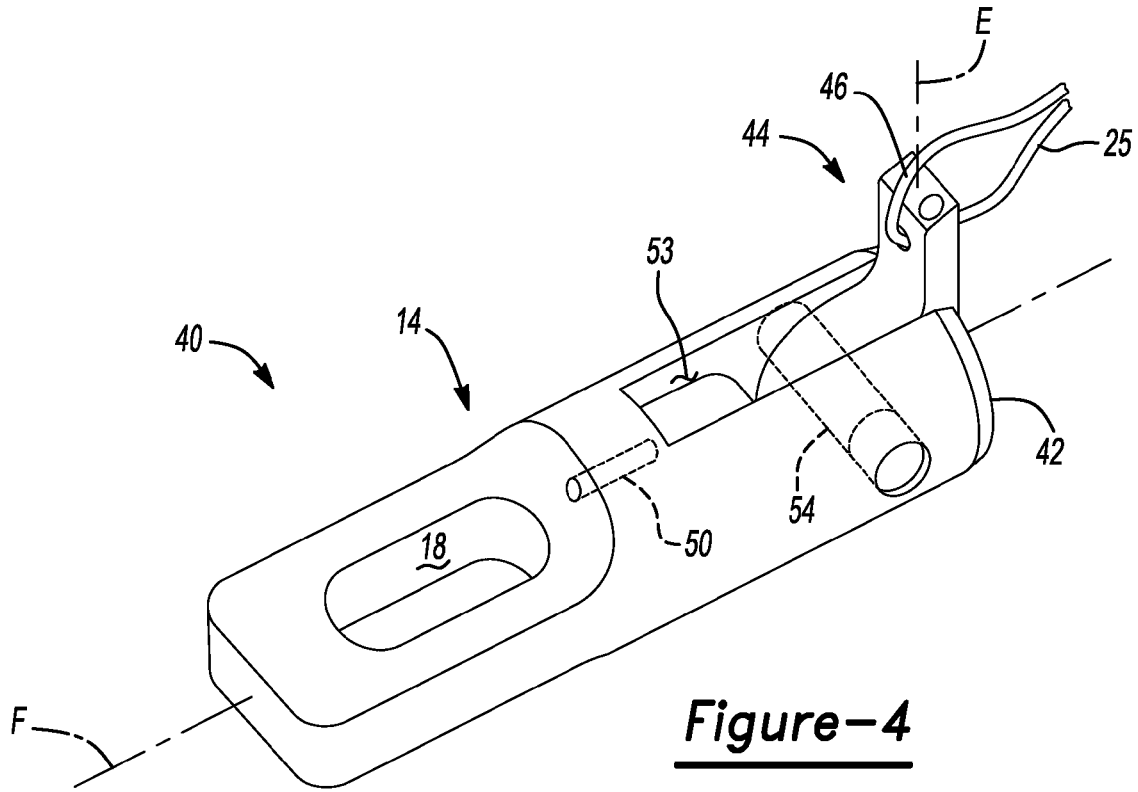
FIG. 4 is a top perspective view of an anchor of FIG. 3 in an activated position.

With reference to FIG. 4, the anchor 40 is illustrated in the operable position and includes the lever arm 44 in an activated position. Again, a longitudinal axis E of the lever arm 44 may be provided substantially perpendicular to a longitudinal axis F of the body 14 of the anchor 40. In the activated position, the strand 25 may be used to move the lever arm 44 to a position that may include a length greater than a radius of the body 14. That is, the actuation portion 46 of the lever arm 44 may extend a distance beyond a circumference or edge of the body 14. As described herein, the actuation portion 46 may be activated to engage a selected portion of the anatomy after the anchor 40 has passed through the selected portion of the anatomy.

In the anchor 10, a pin 30 provides a fulcrum around which the lever arm 12 may rotate. Likewise, the pin 54 provides a fulcrum around which the lever arm 44 may rotate. The pins 30, 54 provide a substantially permanent or at least operably permanent connection between the respective lever arms 12, 44 and the anchors 10, 40. Therefore, the anchors 10, 40 are generally provided as a unit to the operating theater and passed through the selected portions of the anatomy as a single unit. This may eliminate portions which may become loose or disengaged during an operative procedure and allow for a substantial ease of passing the anchor 10, 40 through a selected portion of the anatomy. Therefore, the lever arms 12, 44 may be easily used as operable members of the anchors 10, 40 without worry of them becoming loose or disengaged from the anchor body 14 during an operative procedure.

An exemplary method of performing a procedure using the anchor 40 is illustrated. It will be understood that although the anchor 40 is described as an exemplary way of performing a method of using an anchor, it will be understood that any appropriate anchor may be used. Therefore, it will be understood that the following method described and illustrated as merely exemplary of a method of performing a selected procedure and is not intended to limit the procedure.

Figure 5:
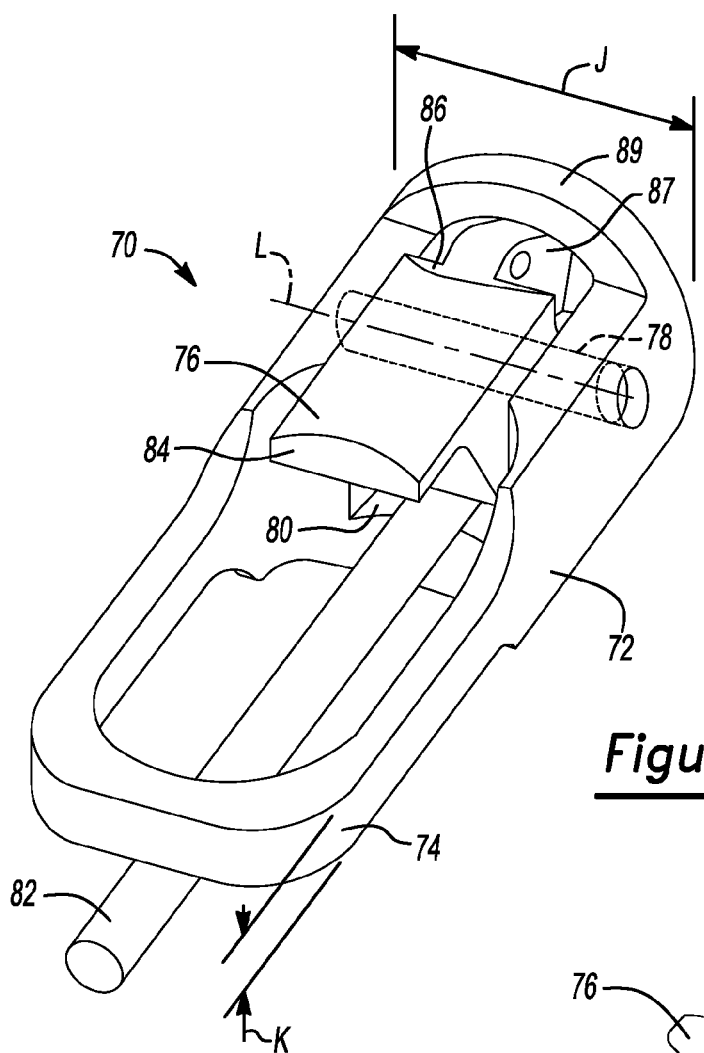
FIG. 5 is a perspective view of an anchor according to various embodiments in an unactivated position.
Figure 6:
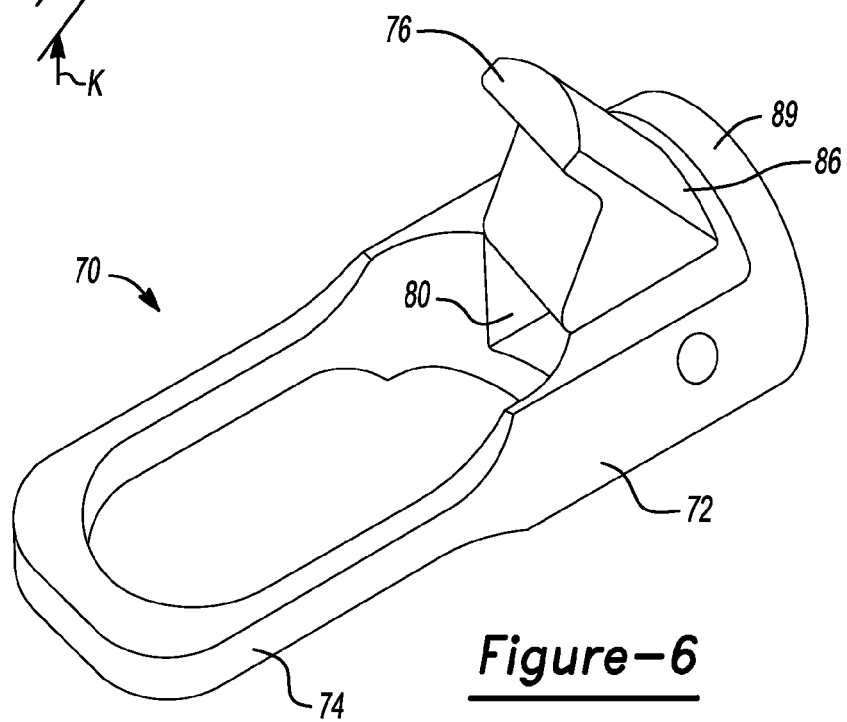
FIG. 6 is a perspective view of an anchor according to various embodiments in an activated position.

With reference to FIGS. 5 and 6, an anchor 70 according to various embodiments is illustrated. The anchor 70 may include portions similar to anchors of various other embodiments and may not be described in detail herein. The anchor 70 generally includes a body portion 72 that defines at least a dimension J. The dimension J, as discussed herein and above, may generally be substantially equivalent to an internal dimension of a bore formed in a bone. Nevertheless, the dimension J may be formed in any appropriate size for selected purposes. For example, as discussed above, the dimension J may be substantially equivalent to an internal diameter of a bore formed in the anatomy such as the anchor 70 may be held substantially tightly within the bore such that the anchor 70 does not move relative to the anatomy or the bore. Nevertheless, it will be understood that the dimension J may be any appropriate dimension.

In addition, the anchor 70 may include an engaging portion 74 that extends from a portion of the body 72. The engaging portion 74 may include a dimension K that is smaller than the dimension J. Therefore, a portion may be positioned relative to the engaging portion 74 such that the dimension of the engaging portion 74 and the portion interconnected therewith does not substantially define a greater dimension than the dimension J. Therefore, it will be understood that the anchor 70 may be provided such that the dimension J is a substantially maximum effective dimension of the anchor 70. For example, the portion interconnected with the engaging portion 74 may be substantially deformable such that it may be deformed to a dimension substantially equivalent to the dimension J without interfering with the effectiveness of the portion interconnected with the engaging portion 74.

The body portion 72 also generally defines a fulcrum or a motion axis L about which a lever arm or engaging portion 76 may move. A fulcrum pin 78 may be provided substantially near the axis L such that the lever arm 76 may rotate relative to the fulcrum pin 78. Nevertheless, it will be understood that the lever arm 76 may move relative to the body 72 or the anchor 70 in any appropriate manner. For example, the lever 76 may substantially slide, snap or the like relative to the body 72 such that the lever arm 76 may be moved from an activated position, as illustrated exemplary in FIG. 5, to an activated position, illustrated exemplary in FIG. 6.

The lever arm 76 is at least partially held within a recess or depression 80 at least partially defined by the body 72. The recess 80 allows the lever arm 76 to be held in a substantially unactivated position such that the lever arm does not substantially change the dimension J of the anchor 70. Therefore, the lever arm 76 may be positioned in a substantially unactivated position and allow the anchor 70 to maintain the substantially maximum dimension in J.

Figure 9:
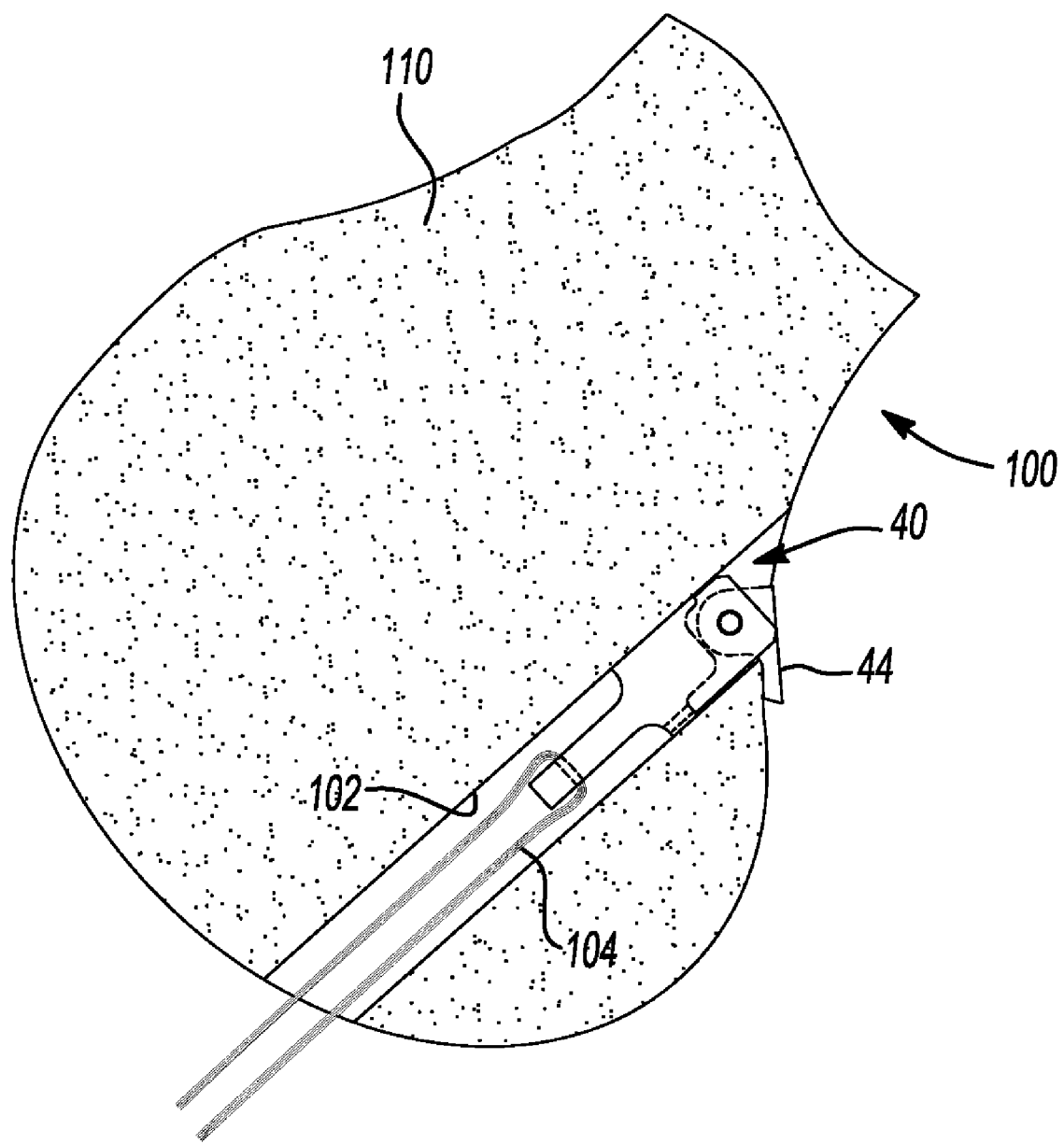
FIG. 9 is an anchor according to various embodiments in a substantially implanted position.

A locking or holding member 82 may be provided to hold the lever arm 76 in a selected position, such as an unactivated position, relative to the anchor 70. The holding portion 82 may also be provided to assist in positioning the anchor 70 in a selected position, such as in a femur 100 (FIG. 9). Therefore, the holding member 82 may be both a locking portion to lock the lever arm 76 in a selected position and to assist in positioning the anchor 70 relative to a portion. Therefore, the engaging portion may be positioned relative to the engaging portion 74 of the anchor 70 and the guiding member 82 used to move the anchor 70 into a selected position.

The lever arm 76 may generally include an engaging portion 84 and a stop portion 86. Moreover, an activating portion 87 may be provided with which an engaging member, such as the flexible strand 25, may be substantially interconnected to activate the lever arm 76.

Therefore, the anchor 70 may be positioned relative to a selected position, such as in a bore of the femur 100, with the guiding rod 82. After positioning the anchor 70 in a selected position, the guide rod 82 may be removed such that the lever arm 76 is no longer substantially locked relative to the anchor 70. The activating portion, such as the flexible strand 25, may then be used to move the lever arm 76 relative to the body 72. The stop portion 86 may engage the anchor body stop portion 89 such that the lever arm 76 substantially rotates to a selected position for implantation.

In addition, the guiding rod 82 may include demarcations 83 or measurements to indicate a depth or distance the anchor member 70 has been moved. Therefore, the anchor 70 may be substantially blindly positioned in the portion of the anatomy, such as the femur 100, using the demarcations on the guiding rod 82 to indicate a selected position of the anchor 70 has been reached.

As discussed herein, the various stop portions 86, 89 may be used to ensure that the lever arm 76 achieves a selected orientation relative to the anatomy after implantation. It will be understood that the position of the lever arm 76 may be any appropriate position and may be provided to ensure an appropriate interaction between the anchor and the anatomy, such as the femur 100.

Figure 7:
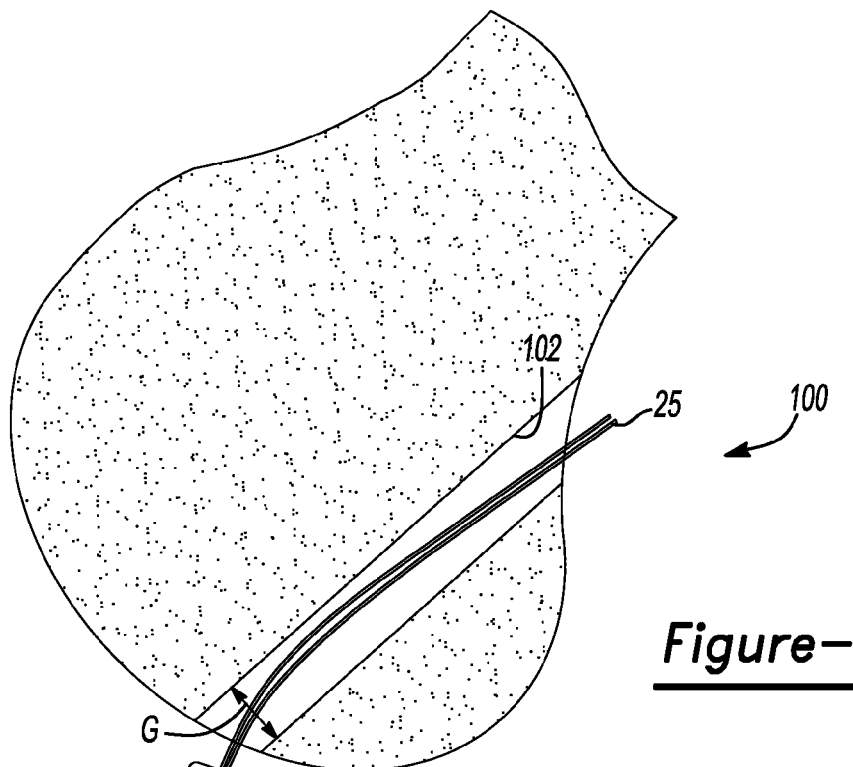
FIG. 7 is an environmental view of a soft tissue anchor according to various embodiments in an unimplanted position.
Figure 8:
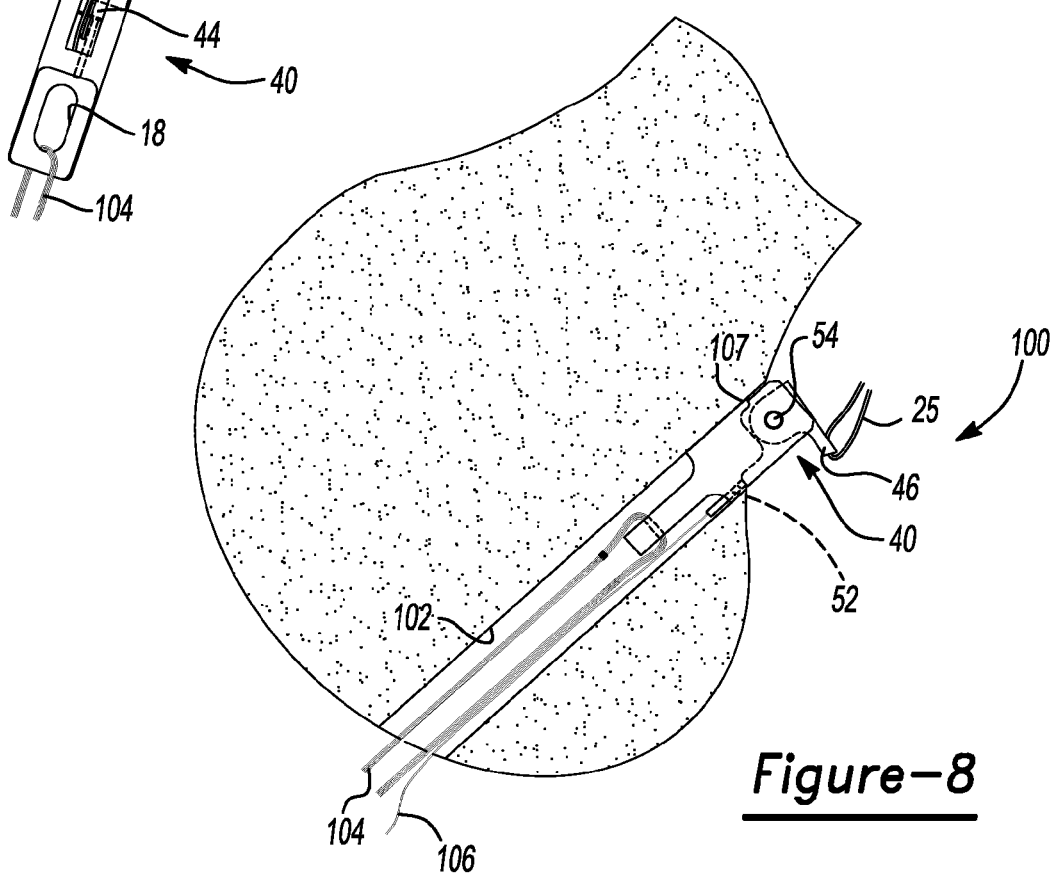
FIG. 8 is a environmental view of an anchor according to various embodiments in an partially implanted orientation.

With initial reference to FIG. 7, procedure may be performed relative to a femur 100. For example, a bore 102, also known as femoral bore 102, may be formed through a portion of the femur. Although the following description relates generally to the replacement of an anterior curiciate ligament (ACL), it will be understood that the various methods and the instruments may be used for any appropriate procedure in an ACL replacement or reconstruction is merely exemplary. In addition, it will be understood that the ACL graft is generally interconnected with the tibial portion, not particularly illustrated, but generally known in the art. Likewise, the femoral bore 102 may be formed using any appropriate instruments, such as drill or reamer. These are generally known in the art and not described in detail herein.

Nevertheless, once the bore 102 is formed, or at any other time appropriate to the procedure, the anchor 40 may be positioned to be moved through the bore 102. The anchor 40 interconnected with the strand 25 may also be interconnected with a graft portion 104. The graft portion 104 may be any appropriate graft portion, such as an allograft or xenograft that may either be natural or synthetic materials. The graft 104 may be interconnected with the anchor 40 prior to a procedure or inneroperatively. Similarly, the strand 25 may be interconnected with the anchor 40 at any appropriate time. The graft portion 104 is generally directly interconnected with the soft tissue engaging portion 16 by being provided through the bore 18. This direct attachment may allow for the graft 104 to be substantially immovably held relative to the anchor 40.

The anchor 40 may be formed of any appropriate materials, as discussed above, including a metal, such as titanium or stainless steel, or other polymer materials. The direct connection of the graft 104 to the anchor 40 allows that the anchor 40, made of a generally rigid material, will not move relative to the graft 104 such that a position of the anchor 40 substantially correlates to a position of the graft 104.

In addition, the bore 102 generally includes a diameter G that is substantially equivalent to the diameter B of the anchor 40. Therefore, the anchor 40 generally includes a substantially close fit with the interior of the bore 102. As discussed herein, this may allow for a selected interconnection of the anchor 40 with the bore 102 for fixation of the anchor 40 relative to the femur 100. Nevertheless, the reduced dimension A of the anchor 40 allows for the graft 104 to be moved through and positioned relative to the bore 102 without substantially binding the graft 104 and the bore 102, as illustrated clearly in FIG. 6.

Nevertheless, once the bore 102 is formed through the femur 100, the strand 25 may be passed through the bore 102. The strand 25 may be passed through the bore 102 in any appropriate manner. For example, a guide wire may be used to assist in forming the bore 102 which may be interconnected with an end of the strand 25 to assist in passing the strand 25 through the bore 102 of the femur 100. Once the strand 25 is passed through the bore 102, the strand 25 may be used to assist in passing the anchor 40 through the femoral bore 102.

The strand 25 is interconnected with the actuation portion 46 of the lever arm 44 of the anchor 40. Therefore, manipulating the strand 25 assists in moving the anchor 40 through the femoral bore 102. The strand may be used to urge the anchor 40 into any appropriate position in the femoral bore 102 or through the femoral bore 102.

With reference to FIG. 6, the anchor 40 may be passed through a substantial portion of the femoral bore 102. The anchor 40 may be passed any appropriate distance through the femoral bore 102, such as a distance great enough to allow the lever arm 44 to be operated. For example, the anchor 40 may be passed a distance through the femoral bore 102 such that a majority of the lever arm 44 is free of the bore 102.

Once the lever arm 44 can be activated, the pin 52 may be removed using any appropriate mechanism. For example, the pin 52 may be interconnected with a suture or trailing line 106 that may be actuated by a user after the anchor 40 is positioned in a selected position. Once the pin 52 is removed, the strand 25 may be used to activate the lever arm 44. In activating the lever arm 44, the lever arm 44 is operably moved to an activated position by rotating a selected distance around the pin 54. Shown particularly in phantom in FIG. 6, the lever arm 44 may be moved such that it extends a distance beyond a circumference of the anchor 40. This allows the lever arm 44 to engage a selected portion of the femur 100 after the lever arm 44 has been activated.

The anchor 40 may include a stop portion 107 that substantially inhibits an extension or rotation of the lever arm 44 beyond a selected portion. Therefore, the lever arm 44 may be moved with the strand 25 until the lever arm 40 engages the stop portion 107. This allows the application or implantation of the anchor 40 to be done substantially without direct viewing of the anchor. Simply, the pin 52 may be removed with the trailing strand 106 and the strand 25 used to pull the lever arm 44 until the lever arm engages the stop 107 and then the anchor 40 may be positioned within the bore 102 at an appropriate location, such as by pulling on the graft 104. Regardless, the stop 107 may also engage the lever arm 44 after the anchor 40 has been positioned within the femur 100 to ensure that the lever arm 44 engages the femur 100 to allow the anchor 40 to substantially engage the femur 100 to hold the graft 104 in a selected position. It will be understood that the stop 107 may be provided in any appropriate manner and simply providing the ledge or fixed stop 107 is merely exemplary.

With reference to FIG. 7, once the lever arm 44 has been activated, the graft 104 may be used to set the anchor 40 in position. The anchor 40 may be pulled adjacent to a portion of the femur 100 such that the lever arm 44 is operable to engage a surface 110 of the femur 100. In this way, the lever arm 44 engages the femur 100 such as the anchor 40 is not able to substantially move a distance through the bore 102 after the lever arm 44 has engaged the surface 110 of the femur 100. The graft 104 may be held within the bore 102 at a selected position due to the interconnection with the anchor 40. The lever arm 44 engages the femur 100 to reduce or substantially eliminate the possibility of the anchor 40 moving back through the femoral tunnel 102.

The anchor 40 may include a circumference that is substantially equivalent to an internal diameter circumference of the femoral tunnel 102. Therefore, the anchor 40, and particularly, for example, the body 14, may engage the femoral tunnel 102 to substantially eliminate any movement of the anchor 40 relative to the femoral tunnel 102. In addition, the body 14 may form an interference fit with the femoral tunnel 102 to assist in fixation of the anchor 40 in the femoral tunnel 102.

The substantially close or interference fit of the body 14 of the anchor 40 with the bore 102 formed in the femur 100 also allows for a substantial fixing of the anchor 40 relative to a selected portion of the femur 100. For example, the body 14 is not able to substantially move within the bore 102 because the bore 102 generally engages at least a portion of the body 14. Therefore, the body 14 is generally not able to lean or tilt within the bore 102. This may allow the lever arm 44 to engage the surface 110 of the femur 100 even though the lever arm 44 may engage the femur 100 only with a portion of the lever arm 44, such as the activation portion 46 which extends to only one side of the fulcrum pin 54, the anchor 40 still allows a substantially immobile position relative to the femur 100.

Therefore, the lever arm 44 may be substantially permanently connected with the anchor body 14 prior to positioning the anchor 40 within the femur 100. The anchor 40 may be provided as a substantially single piece that is passed through a selected portion of the femur 100. Moreover, the lever arm 44 may rotate around a fulcrum pin 54 that is substantially positioned at an end of the lever arm 44. Therefore, the mass of the lever arm 44 may be reduced by providing only the activation section 46 which substantially engages the femur 100.

Therefore, it will be understood that anchors according to various embodiments may pass through a portion of a bore, such as the femoral bore 102, to allow for holding a selected soft tissue, such as an ACL graft 104, relative to a selected portion. Although the ACL graft 104 may be fixed relative to the femoral bore 102, it will be understood that any appropriate soft tissue portion may be fixed or held relative to a selected portion with an appropriate anchor. Simply providing the ACL graph is exemplary of various procedures and implants.

Moreover, in part because the body 14 of the anchor is formed to fit substantially tightly, that is with little movement, within the tunnel 102 the graft 104 is held substantially still within the tunnel 102. This may allow bony ingrowth around and near the graft 104. This may help increase holding power of the graft 104 within the tunnel 102. Thus the body 14 may allow the graft 104 to be held in a selected position within the tunnel 102.

The description of the invention is merely exemplary in nature and, thus, variations that do not depart from the gist of the invention are intended to be within the scope of the invention. Such variations are not to be regarded as a departure from the spirit and scope of the invention.

What is claimed is:

1. A method of fixing a member in a selected region of an anatomy with an anchor member, comprising:
    providing the anchor member including:
        providing a body extending along a first axis including a first end and a second end and having an exterior dimension;
        providing a lever arm interconnected with the body a distance from the first end of the body, movable between an activated position and a non-activated position; and
        providing a connection region spaced a distance from the first end towards the second end of the body;
    providing a holding mechanism that selectively holds the lever arm relative to the body;
    holding the lever arm substantially within the exterior dimension with the holding mechanism;
    releasing the lever arm to move relative to the body;
    moving the lever arm about an axis of motion substantially at an end of the lever arm to the activated position such that a portion of the lever arm moves from within the exterior dimension to extend beyond the exterior dimension to engage a selected portion of the anatomy; and
    contacting a stop portion that extends from the body but is within the exterior dimension;
    wherein the body receives a portion of the lever arm in the non-activated position such that the exterior dimension is substantially maintained.

2. The method of claim 1, wherein holding the lever arm substantially within the exterior dimension in the non-activated position, comprises:
    moving the lever arm to a position within a depression formed in the body;
    sliding the holding mechanism to extend between and contact both the lever arm and a wall forming a portion of the depression within the body.

3. The method of claim 2 further comprising:
    wherein the lever arm extends between a first end and a second end;
    providing the axis of motion at the second end; and
    positioning the second end of the lever arm within the exterior dimension of the body when the first end of the lever arm extends outside of the exterior dimension.

4. The method of claim 3, wherein contacting the stop portion includes moving the lever arm to contact an arch shaped stop portion that extends over the depression formed in the body within the exterior dimension.

5. The method of claim 1, further comprising:
providing the connection region with at least one dimension less than the exterior dimension; and
forming a bore in the anatomy wherein the at least one dimension is less than an internal dimension of the bore formed in the anatomy;
wherein the at least one dimension allows for a graft to be moved through and positioned relative to the bore without substantially binding the graft on a wall of the bore.

6. A method of fixing a member in a selected region of an anatomy with an anchor member, comprising:
providing the anchor member;
engaging a holding member with the anchor member to assist in maintaining the anchor member in a first configuration, including positioning the holding member between a wall that forms a depression in a body of the anchor member and an exterior wall of a lever arm;
moving the anchor member to the selected region of the anatomy at least with assistance of the holding member;
disengaging the holding member from the anchor member to configure the anchor member to a second configuration, including removing the holding member from the depression; and
engaging the selected region of the anatomy with the anchor member to fix the anchor member in the selected region of the anatomy wherein the anchor member includes the body and the lever arm;
rotating the lever arm relative to the body;
providing a lever arm stop portion; and
engaging a body stop portion with the lever arm stop portion to stop rotation of the lever relative to the body, wherein the body stop portion extends over the depression.

7. The method of claim 6, wherein moving the anchor member to the selected region of the anatomy with the holding member includes positioning the anchor member in a selected position with the holding member.

8. The method of claim 7, wherein positioning the anchor member with the holding member includes:
forming a bore in the anatomy; and
pushing the anchor member through the bore to the selected position with the holding member.

9. The method of claim 8, further comprising:
pulling the holding member away from the anchor member and through the bore.

10. The method of claim 6, further comprising:
providing an activating portion extending from the anchor member; and
providing an engaging member interconnected with the activating portion to activate the anchor member to move the anchor member to the second configuration after the holding member has been disengaged.

11. The method of claim 6, further comprising:
providing demarcations on the holding member to indicate an amount of passage of the holding member.

12. The method of claim 11, further comprising:
blindly positioning the anchor member in the anatomy while using the demarcations on the holding member to indicate a position of the anchor member.

13. The method of claim 6, further comprising:
providing the body stop portion to extend as an arch over the depression in the body;
wherein rotating the lever arm includes rotating a portion of the lever arm to include a single end of the lever arm that extends exterior to the body;
wherein when the lever arm engages the body stop portion the body and the lever arm form a substantially L-shape.

14. A method of fixing a member in a selected region of an anatomy with an anchor member, comprising:
providing the anchor member including:
providing a body extending along a first axis including a first end and a second end and an exterior dimension;
providing only a single lever arm interconnected with the body near the first end of the body, movable between an activated position and a non-activated position where the single lever arm is in a depression formed by the body; and
providing a holding member to selectively interconnect the single lever arm and the body and hold the single lever arm substantially within the exterior dimension;
providing an actuating member operably associated with the anchor member;
moving the anchor member relative to the selected region of the anatomy with the actuating member;
after moving the anchor member, releasing the single lever arm to extend a distance beyond the exterior dimension at least by disconnecting the holding member from the single lever arm; and
moving the single lever arm around an axis of rotation positioned substantially at an end of the single lever arm such that a portion of the single lever arm extends beyond the exterior dimension to engage a selected portion of the anatomy;
wherein the body receives a portion of the single lever arm such that the single lever arm is substantially maintained within the exterior dimension in the non-activated position.

15. The method of claim 14, wherein the single lever arm extends between a first end and a second end;
wherein moving the single lever arm includes extending the single lever arm to allow substantially only the first end to extend beyond the exterior dimension to form a substantially L-shape.

16. The method of claim 14, further comprising:
forming a bore in the anatomy; and
engaging the interior surface of the bore with the anchor member to substantially hold the anchor member in a selected position within the bore.

17. The method of claim 14, wherein providing a holding member includes:
sliding the holding member between the single lever arm and the body to contact a wall of the depression and to contact an exterior of the single lever arm to operably hold the single lever arm in a fixed position relative to the body.

18. The method of claim 14, further comprising:
forming a bore in the anatomy with a maximum internal dimension;
providing the anchor member with a maximum exterior dimension substantially equivalent to the maximum internal dimension;
providing the anchor member with a connection region with a transverse dimension less than the maximum exterior dimension;
interconnecting a graft member with the connection region;
after interconnecting the graft member with the connection region, moving the anchor member through the bore; and
fixing the graft member relative to the anatomy by moving the single lever arm about an axis of motion to the activated position;

wherein the transverse dimension allows for the graft to be moved through and positioned relative to the bore without substantially binding the graft on the bore.

19. The method of claim 14, further comprising:
providing the single lever arm extending from a first free end to a second end; and
providing a pivot connection at the second end.

20. The method of claim 19, wherein moving the single lever arm includes extending substantially only the first free end beyond the exterior dimension.

21. A method of fixing a member in a selected region of an anatomy with an anchor member, comprising:
preparing the anchor member including:
providing a body extending along a first axis including a first end and a second end and having a maximum exterior dimension transverse to the first axis;
providing a lever arm connected with the body a distance from the first end of the body, movable between an activated position and a non-activated position;
providing a graft connection region spaced a distance from the first end generally along the first axis towards the second end of the body, wherein the graft connection region has at least one graft connection dimension that is also transverse to the first axis and less than the maximum exterior dimension; and
connecting a graft portion with the graft connection region;
providing a holding mechanism that selectively holds the lever arm relative to the body;
holding the lever arm in the non-activated position substantially within the maximum exterior dimension with the holding mechanism;
forming a bore in the anatomy wherein the at least one dimension is less than an internal dimension of the bore formed in the anatomy, wherein the at least one dimension allows for the graft to be moved through and positioned relative to the bore without substantially binding the graft in the bore;
releasing the lever arm to move relative to the body; and
moving the lever arm around an axis of motion substantially at an end of the lever arm to the activated position such that a single end portion of the lever arm extends beyond the maximum exterior dimension to engage a selected portion of the anatomy;
wherein the body receives a portion of the lever arm such that the exterior dimension is substantially maintained in the non-activated position.

22. The method of claim 21, wherein holding the lever arm in the non-activated position substantially within the exterior dimension comprises:
positioning the lever arm within a depression formed in the body; and
positioning the holding mechanism to extend between and contact both the lever arm and the body within the depression.

* * * * *

UNITED STATES PATENT AND TRADEMARK OFFICE
CERTIFICATE OF CORRECTION

PATENT NO. : 7,776,077 B2
APPLICATION NO. : 12/047048
DATED : August 17, 2010
INVENTOR(S) : Ryan A. Kaiser et al.

It is certified that error appears in the above-identified patent and that said Letters Patent is hereby corrected as shown below:

Title Page, item (73): Assignee: "Medicince" should be --Medicine--

In column 5, line 34; "purposed" should be --purposes--

In column 5, line 36; "form" should be --from--

In column 6, line 24; "as" should be --is--

In column 7, line 55; "curiciate" should be --cruciate--

In column 8, line 6; "inneroperatively" should be --intraoperatively--

In column 11, line 67; insert --of-- before "the body"

In column 11, line 67; insert --to-- after "lever arm"

Signed and Sealed this
Thirteenth Day of March, 2012

David J. Kappos
*Director of the United States Patent and Trademark Office*